United States Patent [19]

Stalling et al.

[11] 4,110,344

[45] Aug. 29, 1978

[54] ADSORBENT FOR POLYNUCLEAR AROMATIC COMPOUNDS

[75] Inventors: David L. Stalling; James N. Huckins; William Allen Smith, all of Columbia, Mo.

[73] Assignee: The United States of America as represented by the Secretary of the Interior, Washington, D.C.

[21] Appl. No.: 843,193

[22] Filed: Oct. 18, 1977

Related U.S. Application Data

[62] Division of Ser. No. 733,500, Oct. 18, 1976.

[51] Int. Cl.$^2$ ............................................ C07D 319/08
[52] U.S. Cl. ............................ 260/340.3; 260/346.71; 260/649 R
[58] Field of Search ............ 260/340.3, 346.71, 649 R

[56] References Cited

U.S. PATENT DOCUMENTS

| 2,658,913 | 11/1953 | Hyman et al. | 260/649 R |
| 3,717,684 | 2/1973 | Notaro et al. | 260/649 R |
| 4,022,805 | 5/1977 | Berger et al. | 260/346.22 |

OTHER PUBLICATIONS

Chem. Abstracts 55:19079e.
Chem. Abstracts 67:120360x.

*Primary Examiner*—Ethel G. Love
*Attorney, Agent, or Firm*—William S. Brown; Donald A. Gardiner

[57] ABSTRACT

An adsorbent composition comprising powdered charcoal on a support of polyurethane foam, and its use for separation of polynuclear aromatic compounds from mixtures containing them.

2 Claims, No Drawings

ADSORBENT FOR POLYNUCLEAR AROMATIC COMPOUNDS

This is a division of application Ser. No. 733,500, filed Oct. 18, 1976.

Powdered charcoal adsorbent has been previously employed for separation and analysis of polynuclear aromatic compounds from mixtures containing them. Such compounds, e.g., dioxins, naphthalenes, and debenzofuranes are highly toxic and concentrations as low as 1 ppm may be very hazardous. An example of such a material is 2,3,7,8-tetrachlorodibenzo-p-dioxin (TCDD) which is found as a contaminant in 2,4,5-trichlorophenol and the herbicides 2,4,5-trichlorophenoxyacetic acid (2,4,5,-T) and herbicide Orange (HO), a 1:1 mixture of the butyl esters of 2,4,5,-T and 2,4-dichlorophenoxyacetic acid (2,4,-D). Such materials and their formation are more fully discussed in U.S. Patent Application Ser. No. 549,127, filed Feb. 11, 1975, now U.S. Pat. No. 4,026,917, the specification of which is hereby incorporated by reference. According to the process of said application, it was found that polynuclear aromatic compounds such as TCDD are strongly adsorbed on coconut charcoal.

Although powdered charcoals have often been found to be efficient adsorbents for the polynuclear aromatic compounds, their use in adsorption columns has been limited because of slow flow rates of feed solutions through the columns, even when the charcoal was mixed with dispersive agents such as celite, sand, and glass powder.

It has now been found, however, in accordance with the present invention, that column flow rates, as well as recoveries of chlorinated polynuclear aromatic compounds, are substantially improved by utilization of polyurethane foam as a support material for the powdered charcoal.

The powdered charcoal may be any type of charcoal, such as that derived from vegetable celluloses or petroleum feedstocks, although specific types of charcoals may give optimum results for adsorption of specific polynuclear aromatic compounds. Suitable particle sizes of the charcoal may range from about $0.1\mu$ to $50\mu$, with optimum sizes varying with specific feed materials, type and dimensions of column employed, temperature, etc.

The polyurethane foams are conventional materials and are prepared by a variety of conventional processes. The precise method of preparation and structure of the polyurethane is not critical, provided that it is characterized by the reticulated structure characteristic of the polyurethane foams, such a structure providing surfaces to which the powdered charcoals strongly adhere. The preferred polyurethane foam is, however, the flexible type which is generally prepared by reaction of polyoxypropylenediols or triols of molecular weights of about 2000 to 4000 with a diisocyanate in the presence of water and a catalyst.

The charcoal-polyurethane foam compositions of the invention are readily prepared simply by admixing the two materials, since, as mentioned above, the powdered charcoals strongly adhere to reticulated foams such as polyurethane foam. The foam may be employed in a finely divided form, e.g., of a particle size of about 0.05 to 0.15mm. Suitable size and shape of the foam particles may be achieved by any conventional means such as shredding, grinding, high speed blending, or combinations of such procedures. Generally, shredding or grinding are accomplished under a solvent such as chloroform or acetone which serves to weaken the polymeric matrix. The foam is then air dried prior to addition of the charcoal.

Preferably, the polyurethane foam is evenly coated with the powdered charcoal. This can be readily achieved by either physical agitation of the foam-charcoal mixture, such as stirring, or by percolation of the foam with the charcoal in an air stream or water. Excess charcoal is then removed by conventional means such as tumbling in an air stream.

The charcoal may also be coated on larger pieces, or sheets, of foam by simply mixing the two in a mixing device such as a commercial washing-drying machine or blender for a suitable period of time, e.g., about 5 to 10 minutes.

Large pieces of foam, or foam sheet, may also be treated by submerging in a water slurry of the charcoal. Air bubbles are expelled from the foam by means of a plunger with a piston-like action in order to permit charcoal penetration of the foam matrix, thus obtaining an essentially uniform impregnation of the foam with the charcoal. The impregnated pieces or sheet are then removed from the charcoal suspension, drip dried, and preferably oven dried under vacuum at a temperature of about 50° to 100° C.

Optimum proportions of charcoal and foam may vary widely depending on the specific type of charcoal and foam, particle size and shape of each, method employed in formation of the charcoal-foam composition and the intended utility of the composition, i.e., the type of separation process to be employed and the specific materials to be separated. Generally, however, the charcoal will constitute about 10 to 20 percent by weight of the charcoal-foam composition.

The adsorbents of the invention find utility in a variety of applications such as column chromatography, air stream filtration, trapping of toxic gases or vapors, abatement of odors, etc. However, they have been found to be particularly useful for separation and analysis of polynuclear aromatic compounds of the type discussed above. Such separations are accomplished by contacting feed mixtures contaminated with the polynuclear compounds with the adsorbents of the invention. The contacting may be by means of any conventional means for contacting fluids with solid adsorbents. E.g., batch type processes in which the adsorbent is added to the feed, and the mixture suitably agitated, may be employed. However, the use of a column containing the adsorbent, through which the feed is percolated, is generally the most convenient and effective means of contacting the adsorbent. Optimum configuration and dimensions of the column may vary greatly with the specific type and amount of feed solution and adsorbent, desired flow rate of feed through the column, etc., and are best determined experimentally.

Where the feed material consists of the above-discussed herbicide compositions, it is usually preferred to dilute the feed with a suitable solvent such as chloroform, ethyl acetate, or acetone. Optimum dilution will generally be sufficient to provide a volume ratio of solvent to feed in the range of about 1:10 to about 1:5.

Generally, ambient conditions of temperature and pressure provide efficient adsorption of the polynuclear compounds. However, elevated temperatures, e.g., about 50° to 100° C, may provide still greater efficiency, but the use of such temperatures is usually limited to procedures in which a diluent is not employed.

Recovery of the polynuclear compounds from the adsorbent may generally be accomplished by treatment of the loaded adsorbent with a suitable solvent. E.g., where a column is employed for adsorption of TCDD, recovery of the TCDD from the adsorbent may be achieved by washing the column with toluene or benzene-toluene mixtures.

The invention will be more specifically illustrated by the following example.

EXAMPLE

A charcoal-polyurethane foam adsorbent was prepared by initially shredding a flexible polyurethane foam under acetone in a Waring blender to reduce the foam to a particle size of about 0.1mm. The foam was then dried and thoroughly mixed in a sorvall omnimixer with 16 percent by weight of powdered charcoal having a particle size of about 0.1–40μ. Excess charcoal was removed by agitating the foam-charcoal in a 200 mesh seive to yield a charcoal-foam adsorbent containing about 14 weight percent charcoal.

An adsorption column was prepared by adding 5 grams of charcoal-foam adsorbent to a 1 cm id glass column to provide a 12 cm bed depth. The adsorbent was then lightly tapped to a depth of 10.0 cm. The column was initially rinsed with 50 ml of ethyl acetate to remove any contaminants from handling. A 10 ml sample of HO (herbicide Orange), containing approximately 100μg of TCDD, was then dissolved in 90 ml of cloroform and percolated through the column at ambient temperature and pressure. Subsequent analysis of the products showed that 97–99 percent of the TCDD was removed from the HO by adsorption on the charcoal-foam adsorbent. The TCDD was recovered for subsequent analysis by percolating the column with 100 ml of 1:1 (v.v) benzene/toluene mixture.

We claim:

1. A process for separation of polynuclear aromatic compounds selected from the group consisting of chlorinated dibenzodioxins, chlorinated naphthalenes, chlorinated dibenzofurans, and mixtures thereof from mixtures containing said compounds comprising contacting said mixtures with an adsorbent consisting essentially of powdered charcoal coated on a support material consisting of polyurethane foam.

2. The process of claim 1 in which the polyurethane foam is in a finely ground form.

* * * * *